United States Patent [19]
Tachikawa

[11] Patent Number: 6,060,620
[45] Date of Patent: May 9, 2000

[54] METHOD FOR MANUFACTURING AN ACYLOXYSILANE COMPOUND HAVING FUNCTIONAL GROUPS BONDED TO SILICON ATOMS VIA SI—C BONDS

[75] Inventor: Mamoru Tachikawa, Kanagawa, Japan

[73] Assignee: Dow Corning Asia, Ltd., Tokyo, Japan

[21] Appl. No.: 09/395,128

[22] Filed: Sep. 14, 1999

[30] Foreign Application Priority Data

Sep. 14, 1998 [JP] Japan .................................. 10-260074

[51] Int. Cl.$^7$ ...................................... C07F 7/08
[52] U.S. Cl. ..................... 556/442; 556/413; 549/215; 554/77; 554/84
[58] Field of Search .................... 556/442, 413; 549/215; 554/77, 84

[56] References Cited

U.S. PATENT DOCUMENTS

| 4,680,365 | 7/1987 | Muller et al. ......................... 556/442 X |
| 5,567,834 | 10/1996 | Bank et al. .............................. 556/442 |
| 5,948,928 | 9/1999 | Siegele et al. ......................... 556/442 |

FOREIGN PATENT DOCUMENTS 9-31414  2/1997  Japan .

*Primary Examiner*—Paul F. Shaver
*Attorney, Agent, or Firm*—William F. Boley

[57] ABSTRACT

A method of manufacturing acyloxysilane compounds having functional groups bonded to a silicon atom via Si—C bonds comprising reacting in a hydrosilation reaction an unsaturated compound (a) selected from the group consisting of (i) styrene or styrene derivative, (ii) vinylsilane compound, (iii) siloxane compound having a vinyl group bonded directly to a silicon atom, (iv) epoxy-functional olefin, (v) diene compound, (vi) allyl compound described by formula $CH_2\!\!=\!\!CHCH_2X$, where X is a halogen atom, an alkoxy group, or an acyloxy group, (vii) olefin compound having a terminal vinyl group, and (viii) acetylene-type compound with a silicon compound (b) that contains hydrogen atom bonded to the silicon atom and acyloxy group in the presence of a platinum catalyst.

4 Claims, No Drawings

METHOD FOR MANUFACTURING AN ACYLOXYSILANE COMPOUND HAVING FUNCTIONAL GROUPS BONDED TO SILICON ATOMS VIA SI— C BONDS

BACKGROUND OF INVENTION

The present invention is a method of manufacturing siloxane or silane compounds which contain acyloxy groups which are important for efficient treatment of surfaces of inorganic solid bodies, for introduction of functional silyl groups or functional siloxanoxy groups into siloxane polymers, organic polymers, or similar polymers, as well as for use as functional groups of siloxanes curable by atmospheric moisture.

Polymers or compounds having silyl groups directly bonded to hydrolyzable functional groups such as alkoxysilyl groups, chlorosilyl groups, etc., find important industrial application as modified silicone-type raw materials used for treating surfaces by hydrolyzing the functional groups followed by the formation of siloxane bonds by dehydration and condensation, or for curing by formation of cross-linking bonds between polymers. As a rule, silyl groups having hydrolyzable functional groups, such as alkoxysilyl groups, chlorosilyl groups, etc., are produced by hydrosilation of unsaturated organic compounds or polymers having unsaturated groups with hydroalkoxysilanes, or hydrochlorosilanes. However, such reactions of hydrosilation of the aforementioned hydrosilane compounds are often characterized by a slow reaction rate, requires a large amount of catalysts, and takes considerable time. Typically, such reactions have poor selectivity and the product is produced as a mixture of isomers. Furthermore in order to maintain catalytic activity, hydrosilation reactions with hydroalkoxysilanes or hydrochlorosilanes often require the presence of oxygen. This is dangerous because it may cause explosion or fire.

Japanese Laid-Open Patent Application (Hei) 9-31414 describes hydrosilation of a vinyl group which is present in polyimide formed by reacting tetracarboxylic acid dianhydride and a diaminopolysiloxaneo having a side vinyl group. The aforementioned hydrosilation reaction is conducted with the use of a hydrosilane represented by the following formula: $X_{3-t}SiH(R^9)_t$, where $R^9$ is an alkyl group having 1 to 6 carbon atoms, X is a hydrolyzable group, except for an alkoxy group, and t is an integer from 0 to 2. Examples of the aforementioned hydrosilanes are methyldiacetoxysilane and triacetoxysilane. Practical examples of the aforementioned publication refer to the use of methyldiacetoxysilane. The present inventors have unexpectedly found that the aforementioned methyldiacetoxysilane and triacetoxysilane possess extremely poor hydrosilation activity with respect to various olefin-type unsaturated compounds and acetylene-type unsaturated compounds, as well as to polyimides having olefin-type unsaturated side groups. In other words, it was unexpectedly found that hydro (monoacyloxy)silanes possess extremely high activity with respect to the last-mentioned olefin-type unsaturated compounds and acetylene-type unsaturated compounds.

It is an object of the present invention to solve the problems associated with hydrosilation involving the use of the aforementioned hydroalkoxysilane, hydrochlorosilane, or hydrodiacyloxysilane and hydrotriacyloxysilane, more specifically the problem associated with low activity during the hydrosilation reaction. Another object is to solve the problem associated with low regio-selectivity in the aforementioned reaction. More specifically, it is an object of the present invention to provide a method for performing the hydrosilation reaction efficiently and economically with regard to the reaction time and catalyst activity, as well as to improve regio-selectivity in the reaction. Another object of the invention is to make it possible to conduct the hydrosilation reaction in an inert environment and under low oxygen partial pressure due to high catalytic activity and extended catalyst activity, thus reducing the danger of explosion and fire in conducting the hydrosilation reaction.

The present inventors have found that silyl compounds can be produced with high yield at a high reaction rate and with high position selectivity by producing functional silane compounds by carrying out a hydrosilation reaction with the use of a platinum catalyst between Si—H functional silane compounds and various olefin-functional or acetylene-functional unsaturated compounds (the aforementioned compounds differ from polyimides derived from diaminopolysiloxane having olefin-type unsaturated side groups). The aforementioned effects are achieved by having in the aforementioned Si—H functional silicon compound one acyloxy group bonded directly to the aforementioned silicon atom. It has been found that the above-described hydrosilation reaction can be rapidly carried out under low partial oxygen pressure or without the presence of oxygen.

SUMMARY OF INVENTION

The present invention is a method of manufacturing acyloxysilane compounds having functional groups bonded to a silicon atom via Si—C bonds comprising reacting in a hydrosilation reaction an unsaturated compound (a) selected from the group consisting of (i) styrene or styrene derivative, (ii) vinylsilane compound, (iii) siloxane compound having a vinyl group bonded directly to a silicon atom, (iv) epoxy-functional olefin, (v) diene compound, (vi) allyl compound described by formula $CH_2=CHCH_2X$, where X is a halogen atom, an alkoxy group, or an acyloxy group, (vii) olefin compound having a terminal vinyl group, and (viii) acetylene-type compound with a silicon compound (b) that contains a hydrogen atom bonded to a silicon atom and an acyloxy group, represented by general formula

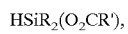

where each R is independently selected from the group consisting of an organic group, a siloxy group, and a siloxanoxy group and R' is a hydrogen atom or an organic group in the presence of a platinum catalyst.

DESCRIPTION OF INVENTION

The present invention is a method of manufacturing acyloxysilane compounds having functional groups bonded to a silicon atom via Si—C bonds comprising reacting in a hydrosilation reaction an unsaturated compound (a) selected from the group consisting of (i) styrene or styrene derivative, (ii) vinylsilane compound, (iii) siloxane compound having a vinyl group bonded directly to a silicon atom, (iv) epoxy-functional olefin, (v) diene compound, (vi) allyl compound described by formula $CH_2=CHCH_2X$, where X is a halogen atom, an alkoxy group, or an acyloxy group, (vii) olefin compound having a terminal vinyl group, and (viii) acetylene-type compound with a silicon compound (b) that contains hydrogen atom bonded to a silicon atom and an acyloxy group, represented by general formula

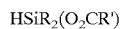 (1), where each R is independently selected from the group consisting of an organic group, a siloxy group, and a siloxanoxy group and R' is a hydrogen atom or an organic group in the presence of a platinum catalyst.

The aforementioned unsaturated compound (a) can be selected from compounds (i)–(viii). As far as these compounds decrease extremely reactivity with the hydro (acyloxy) group containing silicon compound, they may contain in the structure, atom selected from O, N, F, Cl, Br, Si, or S in addition to carbon and hydrogen.

The following are specific examples of aforementioned styrenes and styrene derivatives: styrene-type hydrocarbons, such as styrene, p-methylstyrene, p-ethylstyrene, p-phenylstyrene, and divinylbenzene; halogen-containing styrene, such as p-fluorostyrene, p-chlorostyrene, p-bromostyrene, p-iodostyrene, and p- and n-(chloromethyl) styrene; oxygen- or silicon-containing styrene derivatives, such as p-methoxystyrene and p-trimethylsilylstyrene; nitrogen-containing styrene derivatives, such as p-(diphenylamino) styrene, p-(ditolylamino) styrene, p-(dixylylamino) styrene, and bis (4-vinylphenyl) (4-methylphenyl) amine.

The following are examples of vinylsilane compounds and siloxane compounds having vinyl groups directly bonded to silicon atoms: vinyltrialkylsilanes, such as vinyltrimethylsilane, vinyltriethylsilane, vinyltripropylsilane, and vinyldimethylethylsilane; vinylalkoxysilanes, such as vinyltrimethoxysilane, vinyltriethoxysilane, vinylmethyldiethoxysilane, and vinyldimethylmethoxysilane; vinyl-functional siloxanes, such as 1,3-divinyltetramethylsiloxane, α, ω-divinylpolydimethylsiloxane, and 1,3,5,7-tetravinyl-1,3, 5,7-tetramethylcyclotetrasiloxane; and vinyl-functional silazanes, such as 1,3-divinyltetramethyldisilazane, and 1,3, 5,7-tetravinyl-1,3,5,7-tetramethylcyclotetrasilazane.

The aforementioned epoxy-functional olefins can be, for example, allylglycidyl ether and vinylcyclohexene oxide. The aforementioned diene compounds can be, for example, 1,3-butadiene, isoprene, 1,5-hexadiene, 1,3-octadiene, and 1,3-cyclohexadiene. The aforementioned allyl compound of the following formula: $CH_2=CHCH_2X$ can be exemplified by allyl chloride, allyl acetate, and allyl methacrylate.

The aforementioned olefin compounds having vinyl terminal groups may have either a linear or a branched structure. They also may also be substituted with aromatic hydrocarbon groups. The following are examples of terminal-unsaturated olefin compounds of linear chain type: ethylene, propylene, butene-1, hexene-1, octene-1, and octadecene-1. The following are examples of branched olefin compounds having terminal-unsaturated groups: isobutylene, 3-methylbutene-1, 3,5-dimethylhexane-1, and 4-ethyloctane-1.

The following are examples of the aforementioned olefin compounds having vinyl terminal groups which contain an atom selected from the group consisting of O, N, F, Cl, Br, Si, S: an oxygen-containing allyl compound such as allylmethacrylate; an amine compound containing a vinyl group, such as N-vinylcarbazole; an olefin halide compound, such as 4-chlorobutene-1 and 6-bromohexene-1; silicon-functional olefin compound, such as aryloxytrimethylsilane; sulfur-containing olefin compound, such as allylmercaptane and allyl sulfide. In the case when an aromatic hydrocarbon group is present in the aforementioned olefin compound, the latter can be represented by allylbenzene and 4-vinylbutene-1.

The aforementioned acetylene-type compound may have at its terminal an ethynyl group represented by formula (CH≡C—) or may have within the molecule an ethynylene group of formula (—C≡C—). These compounds may be substituted with aromatic hydrocarbon groups. The following are examples of ethylene-type compounds having an ethynyl group (CH≡C—) at their terminal: acetylene, propyne, butene-1, hexyne-1, and octyne-1. The acetylene-type compounds, which have ethynylene group of formula (—C≡C—) within the molecules, can be exemplified by the following: butyne-2, hexyne-2, hexyne-3, and octyne-4. The acetylene-type compounds having aromatic hydrocarbon groups can be represented by the following: phenylacetylene, 3-phenylpropene, and 4-phenylbutene-1. Examples of the aforementioned acetylene compounds which contain atoms selected from the group containing O, N, F, Cl, Br, Si, S are as follows: 3-methyl-1-butene-3-ol and 3-phenyl-1-butene-3-ol; silicon-containing acetylene-type compound, such as trimethylsilyl adduct of 3-methyl-1-butyne-3-ol (HC≡C—CH(CH$_3$)—O—Si(CH$_3$)$_3$) and trimethylsilyl adduct of 3-phenyl-1-butyne-3-ol (HC≡C—CH (C$_6$H$_5$)—O—Si(CH$_3$)$_3$); and halogen acetylene-type compound, such as propargyl chloride and propargyl bromide.

Silicon compound (b) of the present invention is described by general formula

$$HSiR_2(O_2CR') \qquad (1),$$

where each R is independently selected from the group consisting of an organic group, a siloxy group, and a siloxanoxy group; and R' is a hydrogen atom or an organic group.

When R is an organic group, R can be for example, an alkyl group, alkenyl group, aryl group, halogenated alkyl group, halogenated aryl group, alkoxy group, and aryloxy group. For example, R can be: (1) an alkyl group having 1 to 18 carbon atoms, such as methyl, ethyl, n-propyl, isopropyl, n-butyl, t-butyl, n-pentyl, cyclohexyl, n-octyl, undecyl, and heptadecyl; (2) an alkenyl group having 2 to 18 carbon atoms, such as propenyl and butenyl; (3) an aryl group having 6 to 18 carbon atoms, such as phenyl; (4) a halogenated alkyl group having 1 to 18 carbon atoms (the halogen atom can be F, Cl, or Br), such as a chloromethyl, fluoromethyl, and 3,3,3-trifluoropropyl; (5) a halogenated aryl group having 6 to 10 carbon atoms (the halogen atom can be F, Cl, or Br) such as a p-chlorophenyl; (6) an alkoxy group having 1 to 6 carbon atoms such as methoxy, ethoxy, n-propoxy, i-propoxy, n-butoxy, n-pentyloxy, n-hexyloxy, cyclopentyloxy, cyclohexyloxy, 2-methoxyethoxy, and 2-ethoxyethoxy; and (7) an aryloxy group having 6 to 10 carbon atoms, such as a phenoxy group. If the number of carbon atoms exceeds the recommended range, it would be impractical since the activity of the respective compounds will be reduced.

In the case where R is a siloxy group, R can be for example trimethylsiloxy, triethylsiloxy, phenyldimethylsiloxy, diphenylmethylsiloxy, and (3,3,3-trifluoropropyl) dimethylsiloxy. In the case where R is a siloxanoxy group, R can be, for example, a structure having the main chain in the form of a polydimethylsiloxane having a terminal siloxy group such as a trimethylsiloxy or a terminal capped with —SiH(CH$_3$)(OC(=O)CH$_3$). From the practical point of view, it is recommended that, in terms of a degree of polymerization (i.e., a number-average degree of polymerization) of siloxane units of siloxanoxy groups, the degree of polymerization be below 1,000 and preferably, below 500.

R' is a hydrogen atom or an organic group. When R' is an organic group, it is preferably selected from the following groups: an alkyl group having 1–18 carbon atoms; an aryl group having 6–10 carbon atoms; a halogenated alkyl group having 1–18 carbon atoms; and a halogenated aryl group having 6–10 carbon atoms. The principle of the invention will not be violated if the aforementioned organic group is substituted with oxygen or silicon atoms. The following are examples of the aforementioned compounds: an alkyl group having 1 to 18 carbon atoms, such as methyl, ethyl, n-propyl, isopropyl, t-butyl, n-butyl, n-pentyl, cyclohexyl, n-octyl, undecyl, and heptadecyl; an aryl group having 6 to 10 carbon atoms, such as phenyl, tolyl, xylyl, and naphthyl; a halogenated alkyl group having 1 to 18 carbon atoms, such as chloromethyl, dichloromethyl, trichloromethyl, trifluoromethyl, and 2,2,2-trifluoroethyl; and a halogenated aryl group having 6 to 10 carbon atoms such as p-chlorophenyl.

The following are examples of organic groups where R' comprises an organic group having an oxygen and silicon atom

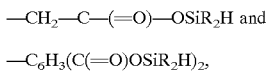

—C$_6$H$_3$(C(=O)OSiR$_2$H)$_2$, where R has the same meaning as has been specified for organic groups in formula (1).

The following are specific examples of compounds represented by formula (1): hydro(formyloxy)silanes, such as dimethylformyloxysilane, diethylformyloxysilane, dipropylformyloxysilane, diisopropylformyloxysilane, methylethylformyloxysilane, methylphenylformyloxysilane, methylpropylformyloxysilane, diphenylformyloxysilane, methylmethoxyformyloxysilane, methylethoxyformyloxysilane, and methyl (trimethylsiloxy) formyloxysilane; hydro(acetoxy)silanes, such as dimethylacetoxy silane, diethylacetoxysilane, dipropylacetoxysilane, diisopropylacetoxysilane, methylethylacetoxysilane, methylphenylacetoxysilane, methylpropylacetoxysilane, diphenylacetoxysilane, methylmethoxyacetoxysilane, methylethoxyacetoxysilane, diethoxyacetoxysilane, and methyl(trimethylsiloxy) acetoxysilane; hydro(propionyloxy) silanes, such as dimethylpropionyloxysilane, diethylpropionyloxysilane, dipropylpropionyloxysilane, diisopropylpropionyloxysilane, methylethylpropionyloxysilane, ethylphenylpropionyloxysilane, methylpropylpropionyloxysilane, biphenylpropionyloxysilane, diphynylpropionyloxysilane, methylmethoxypropionyloxysilane, methylethoxypropionyloxysilane, and methyl (trimethylsiloxy) propionyloxysilane; hydro(butyryloxy) silanes, such as dimethylbutyryloxysilane, diethylbutyryloxysilane, dipropylbutyryloxysilane, diisopropylbutyryloxysilane, methylethylbutyryloxysilane, methylphenylbutyryloxysilane, methylpropylbutyryloxysilane, diphenylbutyryloxy silane, methylmethoxybutyryloxysilane, methylethoxybutyryloxysilane, and methyl (trimethylsiloxy)butyryloxysilane.

The following are specific examples of compounds represented by formula (1): hydro(lauroyloxy)silane, hydro (stearoyloxy)silane, hydro(benzoyloxy)silane, hydro (chloroacetoxy)silane, hydro(dichloroacetoxy)silane, hydro (trichloroacetoxy)silane, hydro(trifluoroacetoxy)silane, hydro(benzoyloxy)silane, and dimethylsilyl esters of isobutyric acid. The aforementioned hydro(lauroyloxy)silanes can be, for example, dimethyl-lauroyloxysilane, methylphenyl-lauroyloxysilane, diphenyl-lauroyloxysilane, methylmethoxy-lauroyloxysilane, methylethoxy-lauroyloxysilane, and methyl (trimethylsiloxy) lauroyloxysilane; the aforementioned hydro(stearoyloxy) silanes can be, for example, dimethyl(methylphenyl) stearoyloxy silane, diphenylstearoyloxysilane, methylmethoxystearoyloxysilane, methylethoxystearoyloxysilane, and methyl- (trimethylsiloxy)stearoyloxysilane; the aforementioned hydro(benzoyloxy)silanes can be, for example, dimethylbenozoyloxysilane, methylphenylbenozoyloxysilane, diphenyl benozoyloxysilane, methylmethoxybenozoyloxy silane, methylethoxybenozoyloxy silane, and methyl (trimethylsiloxy)benozoyloxysilane; the aforementioned hydro (chloroacetoxy)silanes can be, for example, dimethyl (chloroacetoxy)silane, methylphenyl (chloroacetoxy)silane, diphenyl(chloroacetoxy)silane, methylmethoxy (chloroacetoxy) silane, methylethoxy(chloroacetoxy)silane, and methyl(trimethylsiloxy)(chloroacetoxy) silane; the aforementioned hydro(dichloroacetoxy)silanes can be, for example, dimethyl (dichloroacetoxy)silane, methylphenyl (dichloroacetoxy)silane, diphenyl (dichloroacetoxy)silane, methylmethoxy(dichloroacetoxy)silane, methylethoxy (dichloroacetoxy)silane, and methyl(trimethylsiloxy) (dichloroacetoxy)silane; the aforementioned hydro (trichloroacetoxy)silanes can be, for example, dimethyl (trichloroacetoxy)silane, methylphenyl(trichloroacetoxy) silane, diphenyl (trichloroacetoxy)silane, methylmethoxy (trichloroacetoxy)silane, methylethoxy (trichloroacetoxy) silane, and methyl(trimethylsiloxy)(trichloroacetoxy)silane; the aforementioned hydro(trifluoroacetoxy)silanes can be, for example, dimethyl (trifluoroacetoxy)silane, methylphenyl(trifluoroacetoxy)silane, diphenyl (trifluoroacetoxy)silane, methylmethoxy(trifluoroacetoxy) silane, methylethoxy (trifluoroacetoxy)silane, and methyl (trimethylsiloxy)(trifluoroacetoxy)silane; the aforementioned hydro(benzoyloxy)silanes can be, for example, dimethylbenzoyloxy silane, methylphenylbenzoyloxysilane, diphenylbenzoyloxysilane, methylmethoxy benzoyloxysilane, methylethoxybenzoyloxysilane, and methyl(trimethylsiloxy)benzoyloxy silane. In addition to the above, dimethylsilyl esters of the following acids can be used: isobutyric acid, valeric acid, pivalic acid, hexanoic acid, cyclohexanoic carboxylic acid, nonanic acid, toluic acid, naphthoic acid, parachlorobenzoic acid, maronic acid, succinic acid, glutamic acid, terephthalic acid, trimesic acid, or a similar mono-, di-, or tricarboxylic acid.

In view of better availability and for an increase in the production yield, it is preferable to select such silicon compounds with hydrogen atom bonded to the silicon and acyloxy group, which have R in formula (1) in the form of an alkyl group having 1 to 6 carbon atoms, a siloxanoxy group, a siloxy group, or an alkoxy group having 1 to 6 carbon atoms; with R' being preferably a hydrogen atom or an alkyl group having 1 to 6 carbon atoms.

An acyloxysilane compound having functional group bonded to a silicon atom via Si—C bond obtained by the present method may have silane structure or polysiloxane structure, depending on the structure of the silicon compound (b) with hydrogen atom bonded to the silicon and acyloxy group as a starting material. In other words, when R in general formula (1): HSiR$_2$(O$_2$CR') is an organic group, the obtained acyloxysilane compound will have a silane structure, and when R in the aforementioned formula is a siloxy group or a siloxanoxy group, the obtained compound will have a polysiloxane structure.

For the convenience of the description, in the present patent application, the term "acyloxysilane compound having a functional group bonded to a silicon atom via a Si—C bond" covers both acyloxysilanes with aforementioned functional groups and acyloxypolysiloxanes with aforementioned functional groups.

The hydrosilation reaction of the present invention can be carried out at a temperature between 10° C. and 250° C. However, for achieving an appropriate reaction rate and for stable existence of substances participating in the reaction and of the obtained products, it is recommended that the temperature be between 20° C. and 200° C.

The use of solvents is not generally necessary for the purposes of the present invention. However, in order to dissolve some substances, facilitate control of the reaction temperature, and addition of catalytic components, solvents for hydrocarbon-type compounds or solvents for catalytic components can be used. Solvents most suitable for the above purposes are saturated or unsaturated hydrocarbon compounds, such as hexane, cyclohexane, heptane, octane, dodecane, benzene, toluene, xylene, dodecylbenzene; as well as halogenated hydrocarbon compounds, such as chloroform, methylene chloride, chlorobenzene, and orthodichlorobenzene.

Hydrosilation catalysts suitable for the purposes of the present invention are exemplified by a 0-valence platinum-olefin complex, a 0-valence platinum-vinylsiloxane complex, a halogenated bivalent platinum-olefin complex, chloroplatinic acid, and platinum supported on a carrier such as carbon or silica.

The invention will be further described in more detail with reference to practical examples, which, however, should not be construed as limiting the scope of the present invention.

In the description of characteristics of the products given in the examples below, GC designates "gas chromatography", GC-MS designates "gas chromatography—mass spectroscopy". Me stands for "methyl group", OAc stands for "acetoxy group", and Ph stands for "phenyl group".

Acyloxysilane compounds, alkylsilane compounds, and siloxane compounds used in the practical examples given below are either commercially available or synthesized by methods known in the art. Unsaturated compounds were used in the form in which they were commercially obtained. The following is a description of Practical and Comparative examples.

Reference Example 1. (Synthesis of Dimethylacetoxysilane) A 50 mL round-bottom flask was filled with 6.5 g of lithium acetate, and a magnetic stir bar was inserted into the flask; 9.2 g of dimethylchlorosilane was then slowly added, and the contents were stirred overnight at room temperature. After adding 1 g of lithium acetate and stirring for another hour, volatile components were removed under vacuum. The obtained crude product was subjected to distillation under normal pressure, whereby a component having a 91–92° C. boiling point was produced. The composition was confirmed by GC-MS as $HMe_2SiOAc$: m/z (relative intensity): 117 (6.2), 103 (51.9), 75 (56.2), 61 (100), 59 (23.1), 47 (8.6), 45 (30.3).

Practical Example 1. (Reaction between Styrene and Dimethylacetoxysilane) An argon-purged tube was loaded with 1.04 g of styrene, 1.20 g of the dimethylacetoxysilane synthesized in Reference Example 1, and 0.26 g of toluene used as an internal reference. The contents were combined with 6.5 µL of a toluene solution of a complex of 1,3-divinyltetramethyldisiloxane and 0-valence platinum (0.4 Wt. % platinum.) The solution was heated for 2.5 hours at 50° C. GC analysis confirmed that a hydrosilyl compound of styrene was produced with a yield of 88% and that selectivity for the β-adduct was 99.4%. Results of Analysis:

GC-MS: $PhCH_2Me_2SiOAc$: m/z (relative intensity): 207 (1.6), 147 (17.4), 117 (100), 75 (59.2), 61 (9.9), 47 (6.3), 45 (11.5).

Practical Example 2. (Reaction between p-(N,N-di (Xylyl)Amino) Styrene and Dimethylacetoxysilane) A glass tube was loaded with 0.5 g of p-(N,N-di(xylyl) amino) styrene, 0.303 g of the dimethylacetoxysilane, and 1.75 g of toluene. The contents were combined with 6.5 µL of a toluene solution of a complex of 1,3-divinyltetramethyldisiloxane and 0-valence platinum (0.4 Wt. % platinum). The solution was heated for 1.5 hours at 50° C. The GC analysis confirmed that the degree of conversion of p-(N,N-di (xylyl) amino) styrene was equal to 99%, and that a hydrosilyl compound was produced at a yield of 95%. Selectivity for the β-adduct was 99.2%. Results of Analysis:

GC-MS: β-adduct: m/z (relative intensity): 75 (23.7), 117 (9.7), 314 (63.8), 315 (17.0), 445 (100), 446 (36.9), 447 (9.4).

Practical Example 3. (Reaction between Parachlorostyrene and Dimethylacetoxysilane) A glass tube was loaded with 0.28 g of parachlorostyrene, 0.24 g of dimethylacetoxysilane, and 0.07 g of toluene. The contents were combined with 6.5 µL of a toluene solution of a complex of 1,3-divinyltetramethyldisiloxane and 0-valence platinum (0.4 Wt. % platinum). The solution was heated for 3 hours at 50° C. The GC analysis confirmed that the degree of conversion of parachlorostyrene was 72%, and that a hydrosilyl compound was produced with a yield of 68%. Selectivity for the β-adduct was 99.2%. Results of Analysis:

GC-MS (EI): parachorophenethyl dimethylacetoxysilane: m/z (relative intensity) 45 (21), 47 (11), 61 (15), 117 (100), 181 (12), 183 (5.5), 241 (2.6), 243 (1.2), 256 (0.4), 258 (0.2).

Practical Example 4. (Reaction between Divinylbenzene and Dimethylacetoxysilane) A glass tube was filled with 0.13 g of divinylbenzene (80% of mixed para-, meta-compounds, the balance being meta- and para-ethylstyrene), 0.24 g of dimethylacetoxysilane, and 0.033 g of toluene. The contents were combined with 2 µL of a toluene solution of a complex of 1,3-divinyltetramethyldisiloxane and 0-valence platinum (0.4 Wt. % platinum). The solution was heated for 3 hours at 50° C. The GC analysis confirmed that the degree of conversion of divinylbenzene (and ethylstyrene) was equal to 99%, and that a hydrosilyl compound of divinylbenzene was produced with an yield of 95%. The ratio of α, β-adducts to β,β-adducts was 1:17. Results of Analysis:

GC-MS (EI): β,β-adduct, meta-isomer: m/z (relative intensity) 45 (9.8), 47 (7.2), 59 (17), 61 (10), 75 (74), 117 (100), 306 (61), 351 (1.3), 366 (0.9).

Practical Example 5. (Reaction between Octene-1 and Dimethylacetoxysilane) A reaction tube was filled with 0.224 g of octene-1 and 0.24 g of dimethylacetoxysilane, and 0.033 g of toluene. The contents were combined with 10 µL of a toluene solution of a complex of 1,3-divinyltetramethyldisiloxane and 0-valence platinum (0.4 Wt. % platinum). The solution was reacted for 1.3 hours at room temperature. The GC analysis confirmed that the degree of conversion of octene-1 was equal to 97% and that a hydrosilyl compound of octene-1 was produced at a yield of 95%. Results of Analysis:

GC-MS: $C_8H_{17}Si(CH_3)_2OC(O)CH_3$: m/z (relative intensity): 215 (4.9), 117 (100), 75 (55), 61 (15), 59 (7.2), 47 (6.2), 45 (9.5).

Practical Example 6. (Reaction between 1,3-Divinyltetramethyl-1,3-Disiloxane and Dimethylacetoxysilane) A glass tube was filled with 0.186 g of 1,3-divinyltetramethyl-disiloxane, 0.24 g of dimethylacetoxysilane, and 0.047 g of toluene. The contents were combined with 2 μL of a toluene solution of a complex of 1,3-divinyltetramethyldisiloxane and 0-valence platinum (0.4 Wt. % platinum). With exothermic heating, the reaction was completed during 5 minutes. The GC analysis confirmed that the degree of conversion of 1,3-divinyltetramethyl-disiloxane was equal to 99% and that a hydrosilyl compound of divinylbenzene was produced with a yield of 95%. The ratio of α, β-adducts to β,β-adducts was 1:21. Results of Analysis: GC-MS (EI): 1,3-bis (dimethylacetoxysilyl ethyl) tetramethyl disiloxane, β,β-adduct: m/z (relative intensity): 73 (18), 75 (39), 117 (59), 145 (8.5), 161 (13), 191 (8.8), 203 (8.2), 207 (9.0), 219 (14), 231 (12), 235 (100), 236 (26), 237 (14), 277 (38), 278 (9.7), 305 (11), 306 (3.9), 363 (1.3), 364 (0.5).

Practical Example 7. (Reaction between Vinylcyclohexene Oxide and Dimethylacetoxysilane) A glass tube was filled with 0.50 g of vinylcyclohexene oxide, 0.47 g of dimethylacetoxysilane, and 0.12 g of toluene. The contents were combined with 4 μL of a toluene solution of a complex of 1,3-divinyltetramethyldisiloxane and 0-valence platinum (0.4 Wt. % platinum). The solution was heated for 30 minutes at 67° C. The GC analysis confirmed that a degree of conversion of vinylcyclohexene oxide was equal to 99.5%, and that a hydrosilyl compound of vinylcyclohexene oxide was produced with a yield of 97%. Results of Analysis: GC-MS: m/z (relative intensity): 227 (0.2), 199 (0.2), 167 (1.2), 117 (100), 77 (14), 75 (80), 61(12).

Practical Example 8. (Reaction between Allylmethacrylate and Dimethylacetoxysilane) A glass tube was filled with 0.252 g of allylmethacrylate and 0.236 g of dimethylacetoxysilane. The contents were combined with 10 μL of a toluene solution of a complex of 1,3-divinyltetramethyldisiloxane and 0-valence platinum containing (0.4 Wt. % platinum). The solution was heated for 4 hours at 50° C. The GC analysis confirmed that the degree of conversion of allylmethacrylate was equal to 64%, and that a hydrosilyl compound of allylmethacrylate was produced with the yield of 61%. Results of Analysis:

GC-MS: m/z (relative intensity): 229 (9.5), 187 (1.6), 184 (5.4), 169 (2.9), 145 (15.2), 143 (17.8), 117 (100), 75 (86), 69 (56), 47 (8.1), 45 (14.3).

Practical Example 9. (Reaction between Allylchloride and Dimethylacetoxysilane) A glass tube was filled with 0.15 g of allylchloride and 0.24 g of dimethylacetoxysilane. The contents were combined with 2 μL of a toluene solution of a complex of 1,3-divinyltetramethyldisiloxane and 0-valence platinum (0.4 Wt. % platinum). The solution was heated for 4 hours at 50° C. The GC analysis confirmed that the degree of conversion of allylchloride was equal to 56% and that a hydrosilyl compound of allylchloride was produced at a yield of 40%. Results of Analysis:

GC-MS: m/z (relative intensity): 179 (0.1), 153 (0.1), 137 (13.8), 117 (64), 97 (9.4), 95(29), 93 (8.7), 75 (100), 47(15.7), 45 (30.6).

Practical Example 10. (Reaction between α,ω-Divinylpolydimethylsiloxane and Dimethylacetoxysilane) A glass tube was filled with 704 mg of α,ω-divinylpolydimethylsiloxane (degree of polymerization: 9) and 250 mg of dimethylacetoxysilane. The contents were combined with 2 μL of a toluene solution of a complex of divinylsiloxane and 0-valence platinum (0.4 Wt. % platinum content). The mixture was exothermally heated, and 10 minutes after completion of the reaction, the product was naturally cooled. The contents were then subjected to analysis with proton NMR. The results of the analysis showed that almost all vinyl groups of the α,ω-divinylpolydimethylsiloxane disappeared, and that dimethylacetoxysilyl groups were added to the hydrosilyl compound only in β-positions. Results of Analysis: 1H-NMR (d-chloroform): δ (functional group, relative intensity) 2.00 ($CH_3$, 2.937), 0.59–0.65 ($CH_2$, 1,909), 0.39–0.435 ($CH_2$, 2.02), 0.21 ($CH_3$, 5.86), −0.02–0.2 ($CH_3$, 25.14).

Practical Example 11. (Dimethyl Polysiloxane Having Methylacetoxysilyl Function (—SiH($CH_3$)(OC(=O)$CH_3$)) at Terminal. A glass tube was filled with 220 mg of styrene and 590 mg of functional dimethylpolysiloxane having (HSi($CH_3$)(OC(=O)$CH_3$)) on both terminals (degree of polymerization: 6.5). The contents were combined with 4 μL of a toluene solution of a complex of divinylsiloxane and 0-valence platinum (0.4 Wt. % platinum content). The tube was sealed with Teflon tape and heated in an oil bath for 2 hours at 60° C. After cooling, the contents were subjected to analysis with proton NMR. The results showed that styrene was completely consumed and that hydrosilation of the styrene occurred only in β-positions. Results of Analysis: $^1$H-NMR (d-chloroform): δ (functional groups, relative intensity) 0.11–0.20 ($CH_3$, 101.5), 0.33 ($CH_3$, 17.5), 1.18 ($CH_2$, m, 11.4), 2.1 ($CH_3$, s, 17.6), 2.77 ($CH_2$, m, 13.9), 7.2–7.45 ($C_6H_5$, 34.0).

Practical Example 12. (Reaction between Styrene and Methylethoxyacetoxysilane) A glass tube was filled with 213 mg of styrene, 316 mg of methylethoxyacetoxysilane (HSi($CH_3$)($OC_2H_5$)(OC (=O)$CH_3$) (which contained about 10% each of methyldiethoxysilane and methyldiacetoxysilane), and 52 mg of toluene. The contents were combined with 2 μL of a toluene solution of a complex of divinylsiloxane and 0-valence platinum (platinum content: 0.4 Wt. %). The tube was sealed with a Teflon tube and heated for 1 hour at 80° C. in an oil bath. After cooling, the product was subjected to GC and GC-MS analysis. The analyses confirmed that styrene was completely consumed and that the following three phenethyl compounds were formed at a ratio of 1:5:1: phenethylmethyldiethoxysilane (PhC$_2$H$_4$Si (CH$_3$) (OEt)$_2$), phenethylmethylacetoxyethoxysilane (PhC$_2$H$_4$Si(CH$_3$)(OEt)(OAc), and phenethylmethyldiacetoxysilane (PhC$_2$H$_4$Si(CH$_3$) (OAc)$_2$. In all cases, only β-adducts were formed. For verification, an excess of ethanol was added to the mixture, and after heating for 5 hours at 80° C., a GC analysis was carried out. The analysis confirmed a ratio of α-phenethylmethyldiethoxysilane (PhC$_2$H$_4$Si(CH$_3$)(OEt)$_2$) to β-phenethylmethyldiethoxysilane (PhC$_2$H$_4$Si(CH$_3$)(OEt)$_2$) of 1:390. Results of GC-MS Analysis (EI mode, z/m (relative intensity): PhCH$_2$CH$_2$Si(CH$_3$) (OEt)$_2$ (MW=238): 61 (13), 77 (33), 89 (24), 105 (20), 133 (100), 147 (6.6), 177 (10), 223 (15), 238 (5.4). PhCH$_2$CH$_2$Si(CH$_3$)(OEt)(OAc) (MW=252) :77 (30), 105 (54), 147 (100), 163 (2.5), 177 (3.8), 191 (7.4), 207 (2.5), 237 (0.2), 252 (0.2). PhCH$_2$CH$_2$Si(CH$_3$)(OAc)$_2$ (MW=266): 77 (65), 102 (18), 119 (100), 161 (22), 191 (45), 206 (12), 223 (4.6), 251 (0.3), 266 (1.3).

Practical Example 13. (Reaction between Hexene-1 and Dimethylacetoxysilane) A glass tube was filled with 82 mg of hexene-1 and 118 mg of dimethylacetoxysilane. The contents were combined with 2 μL of a toluene solution of a complex of divinylsiloxane and 0-valence platinum (platinum content: 0.4 Wt. %). The contents were exothermally heated and cooled after 10 minutes. Thirty minutes later, the product was subjected to gas chromatography analysis. The analysis confirmed that the conversion of dimethylacetoxysilane was equal to 96%, and that the product of hydrosilation of the hexene-1 was 91% of the peak area (FID detector) under the GC trace. Among the products of the hydrosilation of hexene-1, the ratio of terminal silyl to inner silyl (2-silylhexene) hydrosilation was 19:1. Results of Analysis: GC-MS (EI): 1-hexenyl (dimethyl) acetoxysilane: m/z (relative intensity): 185 (55), 143 (45), 117 (100), 75 (81), 61 (50), 59 (15), 47 (10), 45 (24).

Practical Example 14. (Reaction between Vinyltriethoxysilane and Dimethylacetoxysilane) A glass tube was filled with 380 mg of vinyltriethoxysilane and 236 mg of dimethylacetoxysilane. The contents were combined with 2 μL of a toluene solution of a complex of divinylsiloxane and 0-valence platinum (platinum content: 0.4 Wt. %). The tube was sealed with Teflon tape and a rubber septum, and heated for 2.5 hours in an oil bath at 60° C. After cooling, the product was subjected to gas chromatography analysis. The analysis confirmed that the conversion of dimethylacetoxysilane and vinyltriethoxysilane was 93%, and that the product of hydrosilation of vinyltriethoxysilane was 89% of the peak area (FID detector) under the GC trace. Among the products of hydrosilation of vinyltriethoxysilane, the ratio of terminal silyl (β-adduct) to inner silyl (α-adduct) was 18:1. Results of GC-MS Analysis: (EI mode, z/m (relative intensity): $(EtO)_3SiCH_2Si(CH_3)_2(OAc)(MW=308)$: 45 (21), 47 (7.8), 75 (49), 79 (16), 117 (100), 135 (9.7), 163 (8.4), 177 (17), 219 (5.3), 221 (6.6), 235 (5.0), 262 (2.0), 263 (2.2), 308 (1.0).

Practical Example 15. (Reaction between Allylacetate and Dimethylacetoxysilane) A glass tube was filled with 458 mg of allylacetate and 540 mg of dimethylacetoxysilane. The contents were combined with 5 μL of a toluene solution of a complex of divinylsiloxane and 0-valence platinum (platinum content: 0.4 Wt. %). The tube was sealed with Teflon tape and a rubber septum, and the content was heated for 2 hours in an oil bath at 80° C. After cooling, the product was subjected to gas chromatography analysis. The analysis confirmed that the conversion of dimethylacetoxysilane was 99%, and that the product of hydrosilation of allylacetate occupied 82% of the peak area (FID detector) under the GC trace. Among the products of hydrosilation of allylacetate, the ratio of terminal silyl (γ-adduct) to inner silyl (β-adduct) was 360:1. Results of Analysis: GC-MS (EI): γ-acetoxypropyl dimethylacetoxysilane: m/z (relative intensity): 203 (0.2), 177 (0.2), 161 (6.1), 158 (2.4), 119 (28), 117 (100), 77 (24), 75 (93), 47 (9), 45 (16).

Practical Example 16. (Reaction between Isoprene and Dimethylacetoxysilane) A glass tube was filled with 300 mg of isoprene, 70 mg of dimethylacetoxysilane, and 70 mg of toluene. The contents were combined with 2 μL of a toluene solution of a complex of divinylsiloxane and 0-valence platinum (platinum content: 0.4 Wt. %). The tube was sealed with Teflon tape and a rubber septum and the product was heated for 30 minutes in an oil bath at 80° C. After cooling, the product was subjected to gas chromatography analysis and to $^1$H-NMR analysis. The analyses confirmed that the dimethylacetoxysilane was completely consumed, and that, in addition to the non-reacted isoprene and toluene, a product of monohydrosilation of isoprene and a product of dihydrosilation of isoprene was formed. Among the aforementioned compounds, the products of monohydrosilation occupied about 91% of the peak area (FID detector) under the GC trace, and among the monohydrosilation products determined by means of $^1$H-NMR spectra, the amount of 3-methyl-3-butenyl(dimethyl)acetoxysilane was about 70%. Results of Analysis: GC-MS (EI): 3-methyl-3-butenyl (dimethyl)acetoxysilane: m/z (relative intensity): 45 (25), 47 (13), 61 (16), 75 (100), 111 (20), 117 (83), 153 (1.0), 171 (1.3).

Comparative Example 1. (Reaction between Styrene and Dimethylethoxysilane) A glass tube was filled with 312 mg of styrene and 312 mg of dimethylethoxysilane. The contents were combined with 1 μL of a toluene solution of a complex of divinylsiloxane and 0-valence platinum (platinum content: 0.4 Wt. %). The tube was sealed with Teflon tape and was heated for 30 minutes in an oil bath at 41° C. After cooling, the product was subjected to GC analysis. The analyses confirmed that the conversion of styrene was 36% and that phenethyldimethylethoxysilane was produced at a yield of 27%. The yield of (α-methylbenzyl)dimethylethoxysilane was 8.5%.

Comparative Example 2. (Reaction between p-(N,N-di (Xylyl)Amino) Styrene and Dimethylethoxysilane) A glass tube was filled with 0.5 g of a toluene solution of p-(N,N-di(xylyl)amino)styrene (the solution was formed by dissolving 0.1 g of DXAS (p-(N,N-di (xylyl)amino)styrene) in 0.4 g of toluene) and 0.04 g of dimethylethoxysilane. The contents were combined with 10 μL of a toluene solution of a complex of divinylsiloxane and 0-valence platinum (platinum content: 0.2 Wt. %). The tube was sealed with Teflon tape and heated for 30 minutes in an oil bath at 50° C. After cooling, the product was subjected to GC analysis. The analyses confirmed that the conversion of DXAS was 67%. β-adducts of dimethylethoxysilane with DXAS were produced at a yield of 41% and α-adducts were produced at a yield of 21%.

Comparative Example 3. (Reaction between Divinylbenzene and .Dimethylmethoxysilane) A glass tube was filled with 0.13 g of a divinylbenzene (80%, para-, meta-mixture, the balance being meta- and para-ethylstyrene), 0.21 g of dimethylmethoxysilane, and 0.33 g of toluene. The contents were combined with 2 μL of a toluene solution of a complex of 1,3-divinyltetramethyldisiloxane and 0-valence platinum (platinum content: 0.4 Wt. %). The product was heated for 3 hours at 50° C. Gas chromatography analysis showed that the conversion of divinylbenzene (and ethylstyrene) was 99%, and that the yield of product of hydrosilation of divinylbenzene was 95%. The ratio of α, β-adducts to β,β-adducts was 1:1.36.

Comparative Example 4. (Reaction between Divinyldisiloxane and Dimethylmethoxysilane) A glass tube was filled with 0.186 g of 1,3-divinyltetramethyl-1,3-disiloxane, 0.18 g of dimethylmethoxysilane, and 0.047 g of toluene. The contents were combined with 2 μL of a toluene solution of a complex of 1,3-divinyltetramethyldisiloxane and 0-valence platinum (platinum content: 0.4 Wt. %). The content was heated for 3 hours at 50° C. Gas chromatography analysis showed that the conversion of 1,3-divinyltetramethyl-1,3-disiloxane was 68% and that monosilyl and disilyl compounds of divinylbenzene were produced with the yields of 37% and 30%, respectively. The ratio of α-adducts to β-adducts was 6:1 and the ratio of α, α-adducts to α,β-adducts was 4.4:1.

Comparative Example 5. (Reaction between Styrene and Methyldiacetoxysilane) A glass tube was filled with 210 mg of styrene and 328 mg of methyldiacetoxysilane ($HSi(CH_3)$ $(=O)CH_3)_2$). The contents were combined with 2 μL of a toluene solution of a complex of divinylsiloxane and 0-valence platinum (platinum content: 0.4 Wt. %). The tube was sealed with Teflon tape. The content was heated for 1 hour at 80° C. in an oil bath. After cooling, the product was subjected to gas chromatography analysis, which showed that only non-reacted raw material was detected. After 3-hour heating the results of the analysis were the same.

Comparative Example 6. (Reaction between Styrene and Methyldiethoxysilane) A glass tube was filled with 208 mg of styrene, 270 mg of methyldiethoxysilane (HSi(CH$_3$)OC$_2$H$_5$)$_2$), and 52 mg of toluene. The contents were combined with 2 μL of a toluene solution of a complex of divinlysiloxane and 0-valence platinum (platinum content: 0.4 Wt. %). The tube was sealed with Teflon tape and heated for 1 hour at 50° C. in an oil bath. After cooling, the content was subjected to gas GC analysis, which showed that the conversion of silane and styrene was 90%. A hydrosilyl compound was produced almost quantitatively. The ratio of α-adduct to β-adduct was 42:58.

We claim:

1. A method of manufacturing acyloxysilane compounds having functional groups bonded to a silicon atom via Si—C bonds comprising reacting in a hydrosilation reaction an unsaturated compound (a) selected from the group consisting of (i) styrene or styrene derivative, (ii) vinylsilane compound, (iii) siloxane compound having a vinyl group bonded directly to a silicon atom, (iv) epoxy-functional olefin, (v) diene compound, (vi) allyl compound described by formula CH$_2$=CHCH$_2$X, where X is a halogen atom, an alkoxy group, or an acyloxy group, (vii) olefin compound having a terminal vinyl group, and (viii) acetylene-type compound with a silicon compound (b) represented by general formula HSiR$_2$(O$_2$CR')

where each R is independently selected from the group consisting of an organic group, a siloxy group, and a siloxanoxy group and R' is a hydrogen atom or an organic group in the presence of a platinum catalyst.

2. The method of claim 1, where in the silicon compound R selected from the group consisting of an alkyl group having 1 to 6 carbon atoms, an alkoxy group having 1 to 6 carbon atoms, a siloxy group, and a siloxanoxy group, and R' is an alkyl group having 1 to 6 carbon atoms or a hydrogen atom.

3. The method of claim 1, where the silicon compound is dimethylacetoxysilane.

4. The method of claim 1, where the unsaturated compound is selected from the group consisting of parachlorostyrene, divinylbenzene, octene-1, hexene-1, 1,3-divinyltetramethyl-1,3-disiloxane, vinylcyclohexene oxide, allylmethacrylate, allylchloride, α,ω-divinylpolydimethylsiloxane, styrene, and allylacetate.

* * * * *